United States Patent [19]

Chin et al.

[11] Patent Number: 5,284,999
[45] Date of Patent: Feb. 8, 1994

[54] DNA ENCODING A PITUITARY-SPECIFIC THYROID HORMONE RECEPTOR

[75] Inventors: William W. Chin, Wellesley; Richard A. Hodin, Brookline, both of Mass.; Mitchell A. Lazar, Havertown, Pa.

[73] Assignee: Brigham and Women's Hospital, Boston, Mass.

[21] Appl. No.: 69,643

[22] Filed: May 13, 1993

Related U.S. Application Data

[63] Continuation of Ser. No. 504,806, Apr. 5, 1990, abandoned.

[51] Int. Cl.$^5$ .............................................. C12N 15/12
[52] U.S. Cl. ............................ 435/252.3; 435/64.1; 435/329.1; 536/23.5
[58] Field of Search ................ 435/69.1, 252.3, 320.1; 526/23.5

[56] References Cited

PUBLICATIONS

J. Biol. Chem. 259, 12084–12091, Oct. 10, 1984, Casanova et al. Photoaffinity Labeling of Thyroid Hormone Nuclear Receptors.
Science 240:889–895, May 13, 1988, Evans, The Steroid and Thyroid Hormone Receptor Superfamily.
Science 244:76–69, Apr. 7, 1984, Hodin et al. Identification of a Thyroid Hormone Receptor That is Pituitary Specific.
J. Biol. Chem. 262:3993–3994, Mar. 25, 1987, Mitsuhashi et al. n-Butyrate Increases the Level of Thyroid Hormone Nuclear Receptor in Non–Pituitary Cultured Cells.
Weinberger et al., *Nature* 324:641 (1986).
Sap et al., *Nature* 324:635–640 (1986).
Lazar et al., *Mol. Endocrinol.* 2:893–901 (1988).
Izumo et al., *Nature* 334:539–542 (1988).
Mistuhashi et al., *PNAS* 85:5804∝5808 (1988).
Koenig et al., *PNAS* 85:5034–5035 (1988).
Lazar et al., *Mol. Endocrinolog,* 2:479–484 (1988).
Benbrook et al., *Science* 238:788–791 (1987).
Kaji et al., *Endocrinology* 120(2):537–543 (1987).
Damm et al., *Nature* 339:593–597 (1989).
Koenig, R. J. et al., "Isolation of a cDNA Clone Encoding a Biologically Active Thyroid Hormone Receptor", *Proc. Natl. Acad. Sci. U.S.A.* 85:5031–5035 (1988).
Thompson, C. C. et al., "Identification of a Novel Thyroid Hormone Receptor Expressed In The Mammalian Central Nervous System", *Science* 237:1610–1614 (1987).

Primary Examiner—Robert J. Hill, Jr.
Assistant Examiner—John D. Ulm
Attorney, Agent, or Firm—Sterne, Kessler, Goldstein & Fox

[57] ABSTRACT

The invention relates to the purification and cloning of a receptor for thyroid hormone. The receptor is designated PSTHR and is related to hormone receptors encoded by the genes erbA$\alpha$-1, erbA$\alpha$-2 and erbA$\beta$-1. The gene encoding PSTHR, erbA$\beta$-2, is partially homologous to the erbA$\beta$-1. However, PSTHR differs from the product of erbA$\beta$-1 in that its expression is limited to the anterior pituitary gland. The invention additionally concerns the uses for PSTHR in the diagnosis and therapy of human conditions.

6 Claims, 1 Drawing Sheet

DNA ENCODING A PITUITARY-SPECIFIC THYROID HORMONE RECEPTOR

This application is a continuation of application Ser. No. 07/504,806, filed Apr. 5, 1990, now abandoned.

FIELD OF THE INVENTION

The invention relates to the isolation and purification of a cellular receptor molecule for thyroid hormone. The invention further relates to the cloning of the gene coding for this receptor. The invention also relates to uses for the purified hormone receptor molecule.

BACKGROUND OF THE INVENTION

Thyroid hormone [3,5,3'-triiodothyronine ($T_3$)] exerts diverse metabolic effects on mammalian cells, primarily through its interaction with nuclear receptor proteins of the cells. The $T_3$-receptor complex regulates expression of nearby target genes by transcriptional and posttranscriptional mechanisms.

Nuclear receptors for thyroid hormone have been identified as products of the c-erbA protooncogene. (Weinberger, C. et al., Nature 324:641 (1986); Sap, J. et al., Nature 324:635 (1986)). The c-erbA gene is the cellular counterpart of the viral oncogene v-erbA. Sap et al. (Nature 324:635–640 (1986)) reported that the c-erbA protein is a nuclear protein which functions as a receptor for thyroid hormone, whereas the v-erbA product is located in the nucleus but is defective in binding thyroid hormone. In the rat, three c-erbA-related cDNAs have been described and designated r-erbAα-1, r-erbAα-2 and r-erbAβ-1. The proteins encoded by these genes are classified as alpha or beta forms on the basis of the predicted amino acid sequences and have homologs in man.

The rat r-erbAα-1 and r-erbAα-2 mRNAs represent alternative splice products of a single rat erbAα gene. This gene encodes proteins that are identical for the first 370 amino acids from the N-terminus, and then diverge completely.

The protein encoded by erbAα-1 binds thyroid hormone, whereas the protein encoded by erbAα-2 does not. The thyroid hormone binding domain is included within the divergent regions of the two proteins, and this may account for the difference in binding between the two proteins. (Lazar, M. A. et al., Mol. Endocrinol. 2:893 (1988); Izumo, S. et al., Nature 334:539 (1988); Mitsuhashi, T. et al., Proc. Nat. Acad. Sci. 85:5804 (1988)).

In the rat, expression of the erbA genes appears to be organ-specific. The erbAα-1 mRNA is most abundant in skeletal muscle and brown fat, whereas erbAα-2 is most highly expressed in brain and hypothalamus. The related erbAβ-1 mRNA is highly expressed in kidney and liver. (Koenig, R. J. et al., Proc. Nat. Acad. Sci. 85:5031 (1988)). The protein product of erbAβ-1 mRNA binds thyroid hormone with high affinity.

$T_3$ is an iodine-containing amino acid secreted by the thyroid gland. Thyroid function in turn is regulated by the thyroid-stimulating hormone (TSH) of the anterior pituitary gland, and the rate of TSH secretion by the pituitary is regulated in part by circulating thyroid hormone levels via feedback inhibition.

Thyroid hormone exerts physiological effects throughout the body. Thyroid hormone increases oxygen consumption in almost all metabolically active tissues, with a concomitant increase in nitrogen excretion. If food intake does not compensate for the loss of nitrogen, endogenous protein and fat stores are catabolized and weight is lost. The circulating levels of thyroid hormone are important in regulating physiological activity throughout the body, and inappropriately high or low levels of thyroid hormone are implicated in metabolic disorders.

Hypothyroidism, characterized by low circulating levels of thyroid hormones, is associated with a variety of physiological abnormalities. In children, bone growth is slowed and epiphyseal closure is delayed. In adults, protein catabolism results in muscle weakness and osteoporosis; there are also secondary effects on carbohydrate and cholesterol metabolism, as well as on the nervous system and the skin.

Hyperthyroidism, characterized by high circulating levels of thyroid hormone, is associated with nervousness, weight loss, heat intolerance, and a high basal metabolic rate. In general, the secretion of TSH from the pituitary gland is depressed in hyperthyroidism because of the negative feedback effect of the high circulating thyroxine and triiodothyronine levels.

In a few patients hyperthyroidism has been associated with pituitary resistance to thyroid hormone. (Spanheimer, R. G. et al., Arch. Intern. Med. 142:1283–1286 (1982)). This condition is characterized by elevated levels of thyroid hormone in association with an inappropriately elevated serum TSH level. The pituitary gland plays a unique role in modulating the circulating levels of thyroid hormones through its secretion of TSH.

The ability to regulate TSH production by the pituitary has broad implications for treating conditions and diseases in which the levels of thyroid hormones are important. As TSH production is regulated in part by means of thyroid hormone, the mechanism of thyroid hormone binding in the pituitary is of great importance for controlling pituitary TSH production.

SUMMARY OF THE INVENTION

The invention relates to the isolation and purification of a pituitary receptor for thyroid hormone, designated PSTHR (Pituitary Specific-Thyroid Hormone Receptor). The invention further relates to the cloning of the gene encoding this receptor. The invention also relates to the uses of this receptor in the diagnosis and therapy of human conditions and diseases.

DESCRIPTION OF THE PREFERRED EMBODIMENTS

Figure 1:
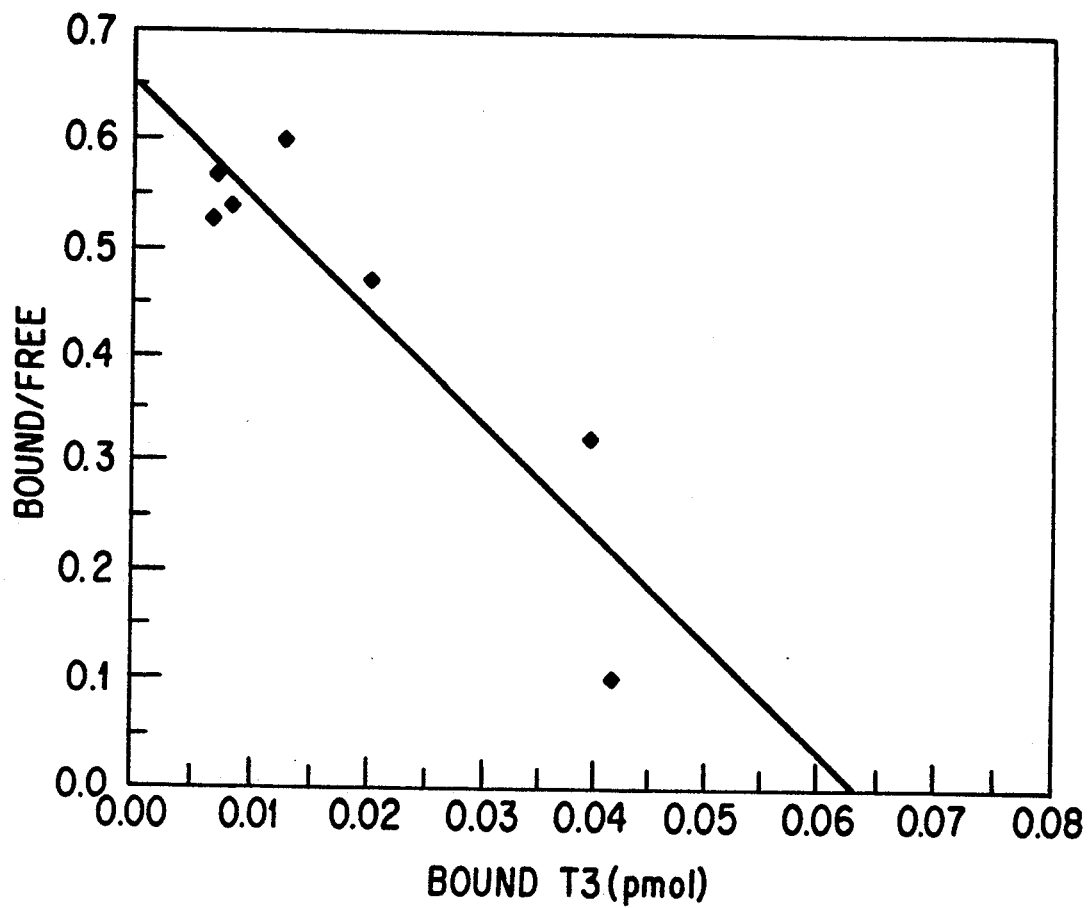
FIG. 1 shows $T_3$ binding of r-erbAβ-2 protein. Labeled $T_3$ (0.1 nM) was incubated with unlabeled $T_3$ at 0 to 100-fold excess.

I. Cloning of Gene Coding for the Thyroid Hormone Receptor Molecule

The present invention relates to the cloning of the gene designated erbAβ-2, which encodes a pituitary-specific receptor for thyroid hormone (PSTHR), and uses for the receptor.

A first step for obtaining a gene sequence which encodes the rat PSTHR comprises obtaining DNA from cells which contain such gene sequences. This DNA is used to prepare a genomic library. Alternatively, CDNA is obtained using cells expressing PSTHR receptors and a CDNA library is prepared.

Techniques for preparing such libraries are disclosed by Maniatis, T., et al. (In: *Molecular Cloning, A Laboratory Manual*, Cold Spring Harbor Laboratories, Cold Spring Harbor, N.Y. (1982)).

To identify and isolate the desired gene sequence, the above-described library is then screened for gene sequences which hybridize to a probe sequence of either the entire rat PSTHR encoding sequence, a sequence complementary to such receptor encoding sequence, or a fragment of either of such sequences. Thus, for example, to isolate a DNA molecule which is capable of encoding a human thyroid hormone receptor, human thyroid hormone receptor expressing cells are used to produce a DNA (or CDNA) library. The members of this library are screened for their ability to hybridize with the above-described rat PSTHR probe sequence using techniques, such as those disclosed by Maniatis, T., et al. (In: *Molecular Cloning. A Laboratory Manual*, Cold Spring Harbor Laboratories, Cold Spring Harbor, N.Y. (1982)), or by Haymes, B. D., et al. (In: *Nucleic Acid Hybridization. A Practical Approach*, IRL Press, Washington, D.C. (1985)).

The DNA probe may be labeled with a detectable group. Such detectable group can be any material having a detectable physical or chemical property. Such materials have been well-developed in the field of immunoassays and in general most any label useful in such ethods can be applied to the present invention. Particularly useful are enzymatically active groups, such as enzymes (see *Clin. Chem.* 22:1243 (1976)); enzyme substrates (see British Pat. Spec. 1,548,741)); coenzymes (see U.S. Pat. Nos. 4,230,797 and 4,238,565)); enzyme inhibitors (see U.S. Pat. No. 4,134,792); fluorescers (see *Clin. Chem.* 25:353 (1979)); chromophores; luminescers (such as chemiluminescers and bioluminescers (see *Clin. Chem.* 25:512 (1979))); specifically bindable ligands; proximal interacting pairs; and radioisotopes. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the latter include, but are not limited to, beta-galactosidase, alkaline phosphatase and peroxidase.

As is generally known to those of ordinary skill, hybridization of the probe to the DNA sequences of the library may be accomplished under a variety of conditions of stringency so as to permit either a stable hybrid to form only between two gene sequences which have very similar sequences (high stringency) or to permit such a hybrid to form between two gene sequences having more divergent sequences (low stringency). Conditions of high stringency employ high temperatures (such as 50°-65° C.) and high concentrations of agents such as formamide (for example 50% formamide). Conditions of low stringency employ lower temperatures (approximately 42° C.) and lower concentrations of agents such as formamide (for example 20-40% formamide) ((Lawler, M. et al., *Bone Marrow Transpl.* 3:473 (1988); Bhattacharya, S. et al., *Ind. J. Med. Res.* 87:144 (1988); Arif, B. M. et al., *Virus Res.* 2:85 (1985); Smith, G. E. et al., *Virol.* 123:393 (1982); Priestly, J. V. et al., *Histochem.* 89:467 (1988); Rohrmann, G. F. et al., *J. Gen. Virol.* 62:137 (1982). When employing hybridization conditions of 42° C. and 20% formamide, two gene sequences having approximately 10% homology can form a stable hybrid (Rohrmann, G. F. et al., *J. Gen. Virol.* 62:137 (1982)).

Once members of the library have been identified which are capable of hybridizing to the probe, it shall be necessary to determine whether they encode the thyroid hormone receptor molecule PSTHR (or a fragment thereof). Such characterization may be conveniently performed in any of several ways. Preferably, the gene sequence can be introduced into a suitable host cell, expressed, and the expressed receptor tested for its ability to bind to thyroid hormone. A gene sequence which expresses a receptor that is capable of binding to thyroid hormone, encodes a thyroid hormone receptor. Alternatively, the expressed molecule can be tested for its ability to bind to antibod (prepared as described below) that is reactive with the thyroid hormone receptor.

In the event that the expressed molecule is unable to bind to thyroid hormone, it may be concluded that the isolated sequence encodes only a fragment of the desired gene sequence. Accordingly, the isolated gene sequence is used to identify and isolate any missing fragments of the desired gene sequence (Bender, W. et al., *J. Supramolec. Struc.* 10(suppl):32 (1979); Chinault, A. C., et al., *Gene* 5:111 (1979); Clarke, L. et al., *Nature* 287:504 (1980)). Once any such sequences have been identified and isolated, it is possible to construct a single gene sequence which is capable of encoding the entire desired receptor molecule using well known methods of recombinant DNA technology.

Amino acid sequence variants of PSTHR can also be prepared by mutations in the DNA. Such variants include, for example, deletions from, or insertions or substitutions of, residues within the amino acid sequence shown in Table II. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these variants ordinarily are prepared by site-directed mutagenesis of nucleotides in the DNA encoding the hormone receptor molecule, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed PSTHR variants screened for the optimal combination of desired activity. Techniques for making substitution mutations at predetermined sites in DNA having a known sequence are well known, for example, site-specific mutagenesis.

Preparation of an PSTHR variant in accordance herewith is preferably achieved by site-specific mutagenesis of DNA that encodes an earlier prepared variant or a nonvariant version of the protein. Site-specific mutagenesis allows the production of hormone receptor molecule variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., DNA 2:183 (1983), the disclosure of which is incorporated herein by reference.

As will be appreciated, the site-specific mutagenesis technique typically employs a phage vector that exists in both single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (U.S.A.)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete hormone receptor molecule sequence) may range generally from about 1 to 10 residues, more preferably 1 to 5 residues. An example of a terminal insertion includes a fusion of a signal sequence, whether heterologous or homologous to the host cell, to the N-terminus of the hormone receptor molecule to facilitate the secretion of mature hormone receptor molecule from recombinant hosts.

The third group of variants are those in which at least one amino acid residue in the hormone receptor molecule, and preferably, only one, has been removed and a different residue inserted in its place.

Most deletions and insertions, and substitutions in particular, are not expected to produce radical changes in the characteristics of the thyroid hormone receptor molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native hormone receptor molecule-encoding nucleic acid, expression of the variant nucleic acid in recombinant cell culture, and, optionally, purification from the cell culture, for example, by immunoaffinity adsorption on a polyclonal anti-hormone receptor molecule column (to adsorb the variant by binding it to at least one remaining immune epitope).

The activity of the cell lysate or purified hormone receptor molecule variant is then screened in a suitable screening assay for the desired characteristic. For example, a change in the immunological character of the hormone receptor molecule, such as affinity for a given antibody, is measured by a competitive type immunoassay. Changes in immunomodulation activity are measured by the appropriate assay. Modifications of such protein properties as redox or thermal stabi l i ty, hydrophobicity, susceptibility to proteolytic degradation or the tendency to aggregate with carriers or into multimers are assayed by methods well known to the ordinarily skilled artisan.

As used herein, the term "hormone receptor" includes the PSTHR receptor molecule. The term "hormone receptors" additionally includes the functional derivatives of such molecules. The term "hormone receptors" additionally includes both glycosylated and unglycosylated forms of any of the above-described molecules.

As used herein, a "functional derivative" of PSTHR is a compound which possesses a biological activity (either functional or structural) that is substantially similar to the biological activity of PSTHR. The term "functional derivatives" is intended to include the "fragments," "variants," "analogs, to or "chemical derivatives" of PSTHR. The term "fragment" is meant to refer to any polypeptide subset of PSTHR. The term "variant" is meant to refer to a molecule substantially similar in structure and function to either the entire PSTHR molecule, or to a fragment thereof. A molecule is said to be "substantially similar" to PSTHR if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical.

The term "analog" is meant to refer to a molecule substantially similar in function to either the entire PSTHR molecule or to a fragment thereof.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980), the disclosure of which is incorporated herein by reference.

"Toxin-derivatized" molecules constitute a special class of "chemical derivatives." A "toxin-derivatized" molecule is a molecule which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the diphtheria toxin, radioisotopic toxins, membrane-channel-forming toxins, etc. Procedures for coupling such moieties to a molecule are well known in the art.

The invention is further directed to methods for screening for hormone agonists or antagonists which bind to the receptor molecule, and to the functional derivatives of such agonists and antagonists. The agonists and antagonists of the present invention may be peptides, proteins, or may be non-proteinaceous organic molecules. All of the above-cited molecules comprise the molecules of the present invention.

As used herein, a "hormone agonist" is a molecule which is capable of binding to a hormone receptor and whose binding to such receptor either (1) mimics the ability of any other molecule to bind to the receptor and to thereby mediate a physiologically significant (i.e. detectable) effect or (2) increases the ability of any other molecule to bind to the receptor and to thereby mediate a physiologically significant effect. An example of a hormone agonist is an organic molecule, or a protein other than LH, which exhibits luteinizing hormone activity.

As used herein, a "hormone antagonist" is a molecule which is capable of binding to a hormone receptor and whose binding to such receptor prevents or attenuates the ability of any other molecule to bind to the receptor and to thereby mediate a physiologically significant (i.e. detectable) effect.

Mammalian tissues contain at least three receptors for thyroid hormones, and these receptor proteins are encoded by DNA molecules with related nucleotide sequences. In the rat, virtually all tissues express mRNAs that are related to the c-erbA protooncogene which encodes a nuclear protein that functions as a receptor for thyroid hormone. The rat erbAα-1 mRNA is most abundant in skeletal muscle and brown fat, whereas rat erbAα-2 mRNA is most highly expressed in brain and hypothalamus. Rat erbAβ-1 mRNA is highly expressed in kidney and liver.

The receptors described above are located in end-target tissues for thyroid hormones, and the effect of thyroid hormone on these tissues in mediated through binding to the receptors. The circulating levels of thyroid hormones in turn are regulated by the pituitary gland, which produces thyroid stimulating hormone in response to a lowered circulating level of thyroid hormone. Thus, thyroid hormone binding in the pituitary will ultimately affect the level of circulating thyroid hormone available to all target tissues.

The novel thyroid hormone receptor described in this application is the product of a unique mRNA found in the anterior pituitary gland. The receptor, designated PSTHR, has no similarity to r-erbAβ-1 or either of the r-erbAα proteins at its amino terminus, but is identical to r-erbAβ-1 from amino acid 147 to the carboxyl end, including the putative DNA- and ligand-binding regions.

Despite the amino acid similarities, r-erbAβ-1 and r-erbAβ-2 mRNAs are differentially regulated by $T_3$ in a pituitary tumor-derived cell line, $GH_3$ cells. In addition, the r-erbAβ-2 mRNA is detected only in the anterior pituitary gland, whereas r-erbAβ-1 mRNA is expressed in kidney and liver.

II. Expression of PSTHR Molecules

DNA or CDNA molecules which encode PSTHR can be operably linked to an expression vector and introduced into a host cell to enable the expression of the receptor molecule by that cell. Two DNA sequences (such as a promoter region sequence and a desired receptor molecule encoding sequence) are said to be operably linked if the nature of the linkage between the two DNA sequences does not (1) result in the introduction of a frame-shift mutation, (2) interfere with the ability of the promoter region sequence to direct the transcription of the desired receptor molecule encoding gene sequence, or (3) interfere with the ability of the desired receptor molecule gene sequence to be transcribed by the promoter region sequence.

A DNA sequence encoding a hormone receptor molecule may be recombined with vector DNA in accordance with conventional techniques, including blunt-ended or stagger-ended termini for ligation, restriction receptor molecule digestion to provide appropriate termini, filling in of cohesive ends as appropriate, alkaline phosphatase treatment to avoid undesirable joining, and ligation with appropriate ligases.

The present invention encompasses the expression of PSTHR in either prokaryotic or eukaryotic cells. Preferred eukaryotic hosts include yeast (especially Saccharomyces), fungi (especially Aspergillus), or mammalian cells (such as, for example, human or primate cells).

Yeast and mammalian cells are preferred hosts of the present invention. The use of such hosts provides substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeast recognize leader sequences on cloned mammalian gene products and secrete peptides bearing leader sequences (i.e., prepeptides). Mammalian cells provide post-translational modifications to protein molecules including correct folding or glycosylation at correct sites.

Mammalian cells which may be useful as hosts include cells of fibroblast origin such as VERO or CHO-KL, and their derivatives. For a mammalian host, several possible vector systems are available for the expression of the desired receptor molecule. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated.

Of interest are regulatory signals which are temperature-sensitive so that by varying the temperature, expression can be repressed or initiated, or are subject to chemical regulation, e.g., metabolite.

The expression of PSTHR in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); the yeast gA14 gene promoter (Johnston, S. A., et al., *Proc. Natl. Acad. Sci. (U.S.A.)* 79:6971–6975 (1982); Silver, P. A., et al., *Proc. Natl. Acad. Sci. U.S.A.* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired receptor molecule does not contain any intervening codons which are capable of encoding a methionine (i.e., AUG). The presence of such codons results either in the formation of a fusion protein (if the AUG codon is in the same reading frame as the desired receptor molecule encoding DNA sequence) or a frame-shift mutation (if the AUG codon is not in the same reading frame as the desired receptor molecule encoding sequence).

The expression of PSTHR can also be accomplished in procaryotic cells. Preferred prokaryotic hosts include bacteria such as *E. coli*, Bacillus, Streptomyces, PseudoNonas, Salmonella, Serratia, etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F−, lambda−, prototrophic (ATCC 27325)), and other enterobacteria (such as *Salmonella typhimurium* or *Serratia marcescens*), and various Pseudomonas species. The prokaryotic host must be compatible with the replicon and control sequences in the expression plasmid.

To express PSTHR in a prokaryotic cell (such as, for example, *E. coli, B. subtilis*, Pseudomonas, Streptomyces, etc.), it is necessary to operably link the PSTHR encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the β-lactamase gene of pBR322, etc. Examples of inducible prokaryotic promoters include the major right and left promoters of bacteriophage λ ($P_L$ and $P_R$), the trp, recA, lacZ, lacI, gal, and tac promoters of *E. coli*, the α-amylase (Ulmanen, I., et al., *J. Bacterial.* 162:176–182 (1985)), the σ-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., N.Y. (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream from the gene-encoding sequence. Such ribosome binding sites are disclosed, for example, by Gold, L., et al. (*Ann. Rev. Microbial.* 35:365–404 (1981)).

The PSTHR encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired receptor molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The CDNA expression vectors incorporating such elements include those described by Okayama, H., *Mol. Cell. Biol.* 3:280 (1983), and others.

Preferred prokaryotic vectors include plasmids such as those capable of replication in *E. coli* such as, for example, pBR322, ColE1, pSC101, pACYC 184, $\pi$VX. Such plasmids are, for example, disclosed by Maniatis, T., et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, N.Y. (1982), pp. 307-329). Suitable Streptomyces plasmids include pIJ101 (Kendall, K. J., et al., *J. Bacteriol.* 169:4177-4183 (1987)), and Streptomyces bacteriophages such as $\phi$C31 (Chater, K. F., et al., In: *Sixth International Symposium on Actinomycetales Biology*, Akademiai Kaido, Budapest, Hungary (1986), pp. 45-54). Pseudomonas plasmids are reviewed by John, J. F., et al. (*Rev. Infect. Dis.* 8:693-704 (1986)), and Izaki, K. (*Jpn. J. Bacterial.* 33:729-742 (1978)).

Once the vector or DNA sequence containing the constructs has been prepared for expression, the DNA constructs may be introduced into an appropriate host. Various techniques may be employed, such as protoplast fusion, calcium phosphate precipitation, electroporation or other conventional techniques. After the fusion, the cells are grown in media and screened for appropriate activities. Expression of the sequence results in the production of the hormone receptor molecule.

The hormone receptor molecules of the invention may be isolated and purified from the above-described recombinant molecules in accordance with conventional methods, such as extraction, precipitation, chromatography, affinity chromatography, electroCON@-phoresis, or the like.

III. The Purification of Thyroid Hormone Receptor PSTHR

The thyroid hormone receptor of the present invention, PSTHR, may be purified by routine adaptation of any of a variety of methods. It is preferable to use the method of Rosemblit, N. et al. (*Endocrinol.* 123:2284-2289 (1988)) which reference is incorporated herein by reference. In accordance with this method, the receptor is isolated by a combination of affinity chromatography, lectin binding and SDS-polyacrylamide gel electrophoresis.

To facilitate recovery, an enriched cellular source of receptor is employed. The preferred source of the thyroid hormone receptor of the invention is the rat pituitary gland, most preferably the anterior pituitary.

To obtain tissue samples, animals are sacrificed, or the desired tissue obtained by surgery. After removal of the receptor-containing tissue from the animal, the tissue is preferably placed in a buffer containing 150 mM NaCl, 20 mM Hepes, pH 7.4 ("Buffer A"). Tissue is preferably maintained at 40° C. Because the proteins may be extremely sensitive to proteolysis, the buffer employed is preferably adjusted to contain 5 mM N-ethylmaleimide, 10 mM phenylmethylsulfonylfluoride, and 10 mM EDTA to inhibit proteolysis (Kellokumpu, S. et al., *Endocrinol.* 116:707 (1985), which reference is incorporated herein by reference).

Tissue samples are dispersed in 10 volumes of Buffer A using a tissue disrupter and then homogenized (preferably using a motor-driven Teflon pestle). Dispersed cellular preparations are centrifuged (for example at 20,000$\times$g for 30 minutes) and resuspended in 5 volumes of Buffer A supplemented to contain 20% glycerol ("Buffer B") and 1% NP-40 (which agents may stabilize the binding activity of the receptors). The preparations are then subjected to high speed centrifugation (100,000$\times$g for 1 hour). The receptor is found in the supernatant of such centrifugation, and can be stored at $-700°$ C.

In a preferred embodiment, the PSTHR molecule may be further purified by affinity chromatography using purified hormone as a ligand. Preparations of highly purified hormone can be obtained commercially. Hormone from such a preparation may be coupled to a (preferably) immobilized resin such as Affi-Gel 10 (Bio-Rad, Richmond Calif.) or the like, by means well known in the art.

The resin is equilibrated in the above-described buffer (preferably supplemented to contain 0.5% NP-40 and 20% glycerol), and the preparation of receptor molecule is placed in contact with it. After sequentially washing the resin with suitable buffers (Buffer B containing 0.5% NP-40; Buffer B containing 0.5M NaCl and 0.1% NP-40; Buffer B containing 0.1% deoxycholate; Buffer B containing 0.1% NP-40; and a solution of 0.1% NP-40, 20% glycerol, and 50 mM glycine, pH 3), receptor molecule is eluted using preferably a buffer of 50 mM glycine, pH 3, 0.1% NP-40, 20% glycerol, and 100 mM NaCl.

In order to assay the eluted material for receptor molecule, an aliquot of sample is incubated in the presence of an excess of labeled thyroid hormone. A preferred method for assaying receptor is described by Roche, P. C. et al., *Endocrinol.* 117:790 (1985), which reference is incorporated herein by reference. After assay, filtration is preferably performed, for example, using the method of Buettner, K. et al., *J. Biol. Chem.* 259:15078 (1984), which reference is incorporated herein by reference. The pH of sample fractions found to contain receptor molecule is preferably neutralized with Tris.

In order to further purify the PSTHR receptor molecule, wheat germ agglutinin purification of PSTHR may be performed. This may conveniently be accomplished by incubating pooled, receptor-containing, affinity purified fractions in the presence of wheat-germ agglutinin-agarose (Vector Laboratories, Burlington, Calif.). After permitting adsorption to occur, the gel may be washed to remove impurities. Receptor may then be eluted from the gel (using, for example, 0.32M N-acetylglucosamine in Buffer B containing 0.1% NP-40, or other buffer) and assayed in the manner described above.

Further purification of PSTHR may be achieved through the use of either analytical or preparative gel electrophoresis. Any suitable method of electrophoresis may be employed such as those of Kim, I.-C. et al. (*J. Biol. Chem.* 262:470 (1987) which reference is incorporated herein by reference), or Laemmli, U.K. (*Nature* 227:680 (1970)). Visualization of the electrophoresed material may be accomplished by silver stain (Wray, W. et al., *Anal. Biochem.* 118:197 (1981 or other means. For preparative gel electrophoresis, the material is preferably concentrated in the manner disclosed by Holloway, P. W. (Anal. Biochem. 53:304 (1973), which reference is incorporated herein by reference) before electrophoresis.

The PSTHR receptor may be further purified by filtration/concentration using, for example, Centricon filter concentrators. The sample may then be further purified by acetone precipitation, followed by gel electrophoresis. The bands obtained from such electrophoresis may be electroeluted, and used to determine the amino acid sequence of the amino ternimus of the protein.

Alternatively, the electroeluted receptor protein may be further precipitated using methanol/chloroform, and digested with an endopeptidase in order to obtain a set of peptide fragments. These fragments can then be sequenced in order to elucidate their amino acid sequence.

Alternatively, the electroeluted receptor molecules may be reprecipitated with acetone, resuspended in buffer (such as Tris, pH 8.5), and cleaved with formic acid/CNBr. The cleavage products can be lyophilized, resolved on a tricine gel, and sequenced.

The identification of a preparation which contains a substantially purified PSTHR permits the amino acid sequence of the receptor molecule to be determined, and further permits the molecule to be produced through the application of recombinant DNA techniques.

Thus, the present invention includes not only substantially purified PSTHR molecules, and methods for use, but also includes the amino acid sequences of these receptor molecules, the genetic sequences coding for these receptor molecules, vehicles containing such genetic sequences, hosts transformed therewith, and hormone receptor molecules produced through transformed host expression.

In order to obtain the amino acid sequence of the PSTHR, the molecules in the substantially purified fractions are recovered by any suitable method. Most preferably, such recovery is accomplished by lectin and hormone affinity chromatography as generally described by N. Rosemblit et al. (*Endocrinology* 123:2284 (1988)), followed by concentration of sample using Centricon-30 (Amicon), and resolution by gel electrophoresis. The recovered molecules may then be sequenced, preferably using an automated sequenator, and the amino acid sequence of the molecule thereby determined. Although any suitable means can be used to determine the sequence of the hormone receptor molecules, it is preferable to determine the sequence using the microsequencing methods of Rodriguez (*J. Chromatog.* 350:217 (1985)). Alternatively, the hormone receptor molecule may be purified by electrophoresis and, after electroelution, cleaved by cyanogen bromide or lysyl-C endopeptidase. The fragments may then be resolved, preferably by HPLC or by tricine gels (H. Shagger et al., *Anal. Biochem.* 166:368 (1987)) followed by electroblotting and gas-phase microsequencing. The sequence of the complete molecule can then be determined and compared with that deduced from the CDNA sequence of PSTHR.

IV. Uses for the Thyroid Hormone Receptor PSTHR

A. Purification of Thyroid Hormone

The PSTHR molecule of the present invention can be used for a variety of biochemical, diagnostic, and therapeutic purposes. A major use of the purified receptor molecule of the invention is in the production and purification of hormone. The capacity of the receptor molecule of the present invention to bind to hormone permits their use in the affinity purification of the hormone.

Thus, for example, the thyroid hormone receptor may be employed to assist in the purification of novel thyroid hormone forms.

B. Anti-Receptor Antibody

The PSTHR molecules of the present invention may be used to induce the formation of anti-hormone receptor antibodies. Such antibodies may either be polyclonal or monoclonal antibodies, or antigen binding fragments of such antibodies (such as, for example, F(ab) or F(ab)$_2$ fragments). Of particular significance to the invention are antibodies (and antigen binding fragments of antibodies) which bind to the extracellular domain of a hormone receptor molecule. The most preferred anti-hormone receptor antibodies (and antigen binding fragments thereof) are those which are capable of preventing or inhibiting the binding of the hormone to its hormone receptor.

Suitable polyclonal antibodies can be obtained by immunizing an animal with an immunogenic amount of the receptor molecule (preferably with an adjuvant, such as Freund's adjuvant).

Alternatively, monoclonal antibodies may be prepared, such as by immunizing splenocytes with a particular receptor and then fusing an immunized cell with a myeloma cell (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563-681 (1981)) in order to obtain a hybridoma cell that secretes an anti-receptor monoclonal antibody.

Of special interest to the present invention are antibodies which are produced in humans, or are "humanized" (i.e. non-immunogenic in a human) by recombinant or other technology such that II they will not be antigenic in humans, or will be maintained in the circulating serum of a recipient for a longer period of time.

Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041-1043 (1988); Liu, A. Y. et al., *Proc. Natl. Acad. Sci. U.S.A.* 84:3439-3443 (1987); Liu, A. Y. et al., *J. Imunol.* 139:3521-3526 (1987); Sun, L. K. et al., *Proc. Natl. Acad. Sci. U.S.A.* 84:214-218 (1987); Nishimura, Y. et al., *Canc. Res.* 47:999-1005 (1987); Wood, C. R. et al., *Nature* 314:446-449 (1985)); Shaw et al., *J. Natl.Cancer Inst.* 80:1553-1559 (1988). General reviews of "humanized" chimeric antibodies are provided by Morrison, S. L. (*Science*, 229:1202-1207 (1985)) and by Oi, V.T. et al., *BioTechnigues* 4:214 (1986)).

Suitable "humanized" antibodies can be alternatively produced ad described by Jones, P. T. et al., *Nature* 321:552-525 (1986); Verhoeyan et al., *Science* 239:1534 (1988), and Beidler, C. B. et al., *J. Immunol.* 141:4053-4060 (1988), or by the methods disclosed in U.S. Pat. Nos. 4,816,397 and 4,816,567, which references are incorporated herein by reference.

C. Diagnostic Uses

In addition to their use in the purification of hormone, the PSTHR molecules of the present invention may be used as the basis for assays of hormone activity. Importantly, since such an assay measures a physiologically significant binding event (i.e. that of a hormone to its receptor and undergoing a detectable change (such as phosphorylation, cleavage, chemical modification, etc.)) it is likely to be both more sensitive and more accurate than immunoassays (which detect the physiologically non-significant binding of hormone to antihormone antibody). Moreover, the thyroid hormone receptor molecules are capable of distinguishing their respective hormones from other hormones with greater specificity than antibodies (which may cross react with structurally similar molecules).

Although more sensitive and accurate than antibodies, the receptor molecules of the invention can be used to assay hormone levels in a sample in the same ways in which antibodies are used.

The anti-receptor antibodies of the present invention may also be used for diagnostic purposes such as to measure the expression and function of a patient's hormone receptors. The anti-receptor antibodies can also be used in imaging in order to characterize tissue, or to define the presence and site of metastasized receptor-expressing cells.

For diagnostic purposes, the receptors and anti-receptor antibodies can be used in accordance with immunoassay technology. Examples of immunoassays are described by Wide at pages 199-206 of *Radioimmune Assay Method*, edited by Kirkham and Hunter, E. and S. Livingstone, Edinburgh, 1970.

Thus, in one embodiment, receptor molecules can be detectably labeled and incubated with a sample, and the amount of receptor molecule bound to the sample can be ascertained. In a second embodiment, antibody to the receptor, or to the hormone, can be used in order to create a "pseudo-sandwich immunoassay." In one such assay (a "forward" assay), a sample suspected of containing hormone can be incubated in the presence of an immobilized anti-hormone antibody. Solubilized, detectably labeled, hormone receptor molecules can be added to the reaction mixture, and the amount of hormone determined by measuring the amount of bound receptor.

As will be evident to those of ordinary skill, various alternative assays can also be devised. The assay may be a simple "yes/no" assay to determine whether hormone is present or may be made quantitative by comparing the measure of labeled molecule with that obtained for a standard sample containing known quantities of hormone.

In another type of assay, which may also be useful with the antigens of the present invention, "simultaneous" and "reverse" assays are used. A simultaneous assay involves a single incubation step as the antibody (or receptor) bound to the solid support and labeled receptor (or antibody) are both added to the sample being tested at the same time. After the incubation is completed, the solid support is washed to remove the residue of fluid sample and uncomplexed labeled antibody. The presence of labeled molecules associated with the solid support is then determined as it would be in a conventional sandwich assay.

In the "reverse" assay, stepwise addition first of a solution of labeled molecule (either receptor or antibody) to the fluid sample followed by the addition of unlabeled molecule (either antibody or receptor) bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the simultaneous and forward assays.

As explained above, the hormone assays of the present invention require that at least one molecule be labeled with a "reporter molecule." Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Suitable radioisotopic labels are well known in the art.

Examples of suitable non-radioactive isotopic labels include $157_{Gd}$, $55_{Mn}$, $162_{Dy}$, $52_{Tr}$, $56Fe$, etc.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1-31 (1976)), and Schurs, A. H. W. M., et al. (*Clin. Chim. Acta* 81:1-40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

In the practice of the present invention, enzyme labels are a preferred embodiment. No single enzyme is ideal for use as a label in every conceivable assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, mal ate dehydrogenase, and glucose-6-phosphate dehydrogenase. Urease is among the more preferred enzyme labels, particularly because of chromogenic pH indicators which make its activity readily visible to the naked eye.

Quantification of nucleic acid molecules which encode the hormone receptor molecule (or a fragment thereof) can be used to determine the extent and rate of the expression of the hormone receptor in the cells of a patient. To accomplish such an assay, a sample of a patient's cells is treated, via in situ hybridization, or by other suitable means, and analyzed to determine whether the sample contains mRNA molecules capable of hybridizing with the nucleic acid molecule.

D. Identification of PSTHR Antagonists and Agonsits

The availability of the PSTHR receptor permits its use in the screening, identification and characterization of agonists and antagonists of thyroid hormone.

A hormone agonist may either be a molecule which increases the physiological effect caused by a hormone's interaction with its receptor, or a molecule which is capable of itself mediating any physiological effect which results from the interaction of thyroid hormone and the PSTHR receptor.

To identify agonists which increase the effect of thyroid hormone, one may assay the capacity of a putative agonist for its ability to enhance the capacity of hormone to bind to PSTHR. Agonists which mimic the activity of a hormone can be identified by their capacity to bind to the receptor molecule, and to mediate a physiologically significant effect which is a characteristic of the interaction of thyroid hormone and PSTHR. Hormone agonists can be used to treat individuals suffering from an inadequate production of hormone, for example, individuals suffering from hypothyroidism.

The availability of PSTHR molecules al so permits the identification of thyroid hormone antagonists. As discussed above, hormone antagonists prevent or attenuate the ability of a hormone to interact with its receptor and thereby mediate a physiologically significant (i.e. detectable) effect. Thyroid hormone antagonists can be identified by their ability to prevent or attenuate the binding of thyroid hormone to PSTHR molecules. The hormone antagonists can be used to decrease the physiological response to PSTHR in an individual. Hormone antagonists may, therefore, be used to treat conditions, such as hyperthyroidism, resulting from the overproduction of a particular hormone.

One class of agonists and antagonists of special concern to the present invention are immunoglobulin agonists or antagonists. The anti-receptor antibodies described above may be tested to determine whether their binding to receptor impairs or prevents the ability of the receptor to bind to hormone molecules. Antibodies having such a capability are hormone antagonists, and may be used, in the same manner as the hormone receptor molecule, to treat individuals suffering from the excessive production of hormone.

Similarly, the anti-receptor antibodies described above may be tested to determine whether their binding to a receptor mimics the binding of a hormone to that receptor. Antibodies having such a capability are hormone agonists, and may be used to treat individuals suffering from a deficiency of hormone production.

Immunoglobulin agonists and antagonists of thyroid hormone can be labeled with toxins and used in the treatment of cancer. Thus, for example, a toxin-derivatized agonist or antagonist of thyroid hormone would be able to bind to the thyroid hormone receptor on malignant cells (or any cells which express the receptor), and thereby provide a means for killing such cells.

E. Identification of PSTHR-Specific Ligands

The thyroid hormone receptor of the invention may be used to screen molecules, or ligands, for their ability to bind to PSTHR, but not to other thyroid hormone receptors. Once identified, such ligands would be of use in effecting biochemical changes in the anterior pituitary without also causing changes in other tissues having thyroid hormone receptors.

Having now generally described the invention, the same will be more readily understood through reference to the following examples which are provided by way of illustration, and are not intended to be limiting of the present invention, unless specified.

EXAMPLES

Example 1

Cloning of a gene encoding PSTHR

RNA was prepared from $GH_3$ cells grown in Dulbeccol's modified Eagle's medium (DMEM) supplemented with 10% fetal calf serum by the method of Chirgwin et al. (*Biochemistry* 18:5294–5299 (1980)).

Two rat $GH_3$ cell cDNA libraries as described in Lazar, M. A. (*Molecular Endocrinology* 2:893–901 (1988)) and Lazar et al., (*Molecular Endocrinology* 2:479–484 (1988)) were initially screened with a fragment from the r-erbAα-2 CDNA clone and subsequently with a 5' fragment from a non-full-length r-erbAβ-2 CDNA clone. Three positive clones corresponding to the r-erbAβ-2 mRNA were obtained.

The cDNA inserts were subcloned into the vector Bluescript (Stratagene) and sequenced by the dideoxy method of Sanger et al. (*Proc. Nat. Acad. Sci. U.S.A.* 74:5463 (1977)). Restriction fragments from two overlapping cDNAs were fused to construct a full-length r-erbAβ-2 clone.

The sequence of the full-length cDNA for PSTHR is shown in Table I. An in-frame stop codon is underlined. Amino acid designations begin at the first potential initiator methionine. The deduced amino acid sequence is shown in Table II.

EXAMPLE II

Expression of PSTHR molecules

The r-erbAβ-2 cDNA insert was subcloned into the vector Bluescript and transcribed into RNA, which was translated in reticulocyte lysates. A protein of approximately 62 kD was produced, in agreement with that predicted from the nucleotide sequence.

The r-ErbAβ-2 protein bound $T_3$ with an affinity constant of 1.1±0.4 nM (mean±SEM), which is similar to that of the endogenous receptor. Competition experiments with thyroid hormone analogs showed that the affinity of the r-ErbAβ-2 protein was greatest for 3,5,3'-triiodothyrocetic acid (triac) followed by $T_3$, $T_4$, and $rT_3$, the same as that of the r-ErbAβ-1 protein.

TABLE I coding region begins ↓

| 10 | 20 | 30 | 40 | 50 | 60 |
|---|---|---|---|---|---|
| GCGAAC<u>TAGG</u> | CTGCTGGGCT | GCTGGTGGTT | ATTCATCCCC | TCTCTTGTTT | C[ATGTGTATG |
| 70 | 80 | 90 | 100 | 110 | 120 |
| GATGTACGCT | GTCCCAGTAT | ATGCACTGCT | CCGGGGAGCA | GGGGGCTGGC | AAGTGCGTGC |
| 130 | 140 | 150 | 160 | 170 | 180 |
| ATGGAGCGTG | TGTGTATATG | TAAAGCAGGA | CTGCACCTGG | ATACCAAAAT | GAACTACTGC |
| 190 | 200 | 210 | 220 | 230 | 240 |
| GTGCCAGAGG | TACACGAAGT | GTGCCCAGCT | GCCGGCAGCA | ACCGTTACAT | GCAGGTCACT |
| 250 | 260 | 270 | 280 | 290 | 300 |
| GACTACCTCG | CGTATCTGGA | AGACAGTCCG | GCTTACAGTG | GCTGCGATGT | CCAAGCTGTG |
| 310 | 320 | 330 | 340 | 350 | 360 |
| CCCGGTAGCA | GCATATATCT | GGAACAGGCC | TGGACTCTGA | ATCAGCCTTA | TACCTGTAGT |
| 370 | 380 | 390 | 400 | 410 | 420 |
| TACCCTGGAA | ACCTGTTTAA | AAGCAAGGAC | TCTGACTTGG | ACATGGCCCT | GAGTCAGTAC |
| 430 | 440 | 450 | 460 | 470 | 480 |
| AGCCAGCCTG | CACATCTCCC | CGAAGAAAAG | CCTTTTCCTC | AAGTGCGGTC | GCCTCCGCAC |
| 490 | 500 | 510 | 520 | 530 | 540 |
| TCACACAAAA | AAGGGTATAT | CCCCAGCTAT | CTAGACAAGG | ATGAGCTCTG | CGTAGTGTGC |
| 550 | 560 | 570 | 580 | 590 | 600 |
| GGGGACAAAG | CCACGGGGTA | CCACTATCGC | TGCATCACCT | GTGAAGGCTG | CAAGGGTTTC |
| 610 | 620 | 630 | 640 | 650 | 660 |
| TTTAGAAGAA | CCATTCAGAA | AAGTCTCCAT | CCATCTTACT | CCTGTAAATA | TGAAGGGAAG |
| 670 | 680 | 690 | 700 | 710 | 720 |
| TGCATCATAG | ACAAAGTCAC | CCGTAACCAG | TGCCAGGAAT | GTCGCTTTAA | GAAATGCATC |
| 730 | 740 | 750 | 760 | 770 | 780 |
| TATGTTGGCA | TGGCAACAGA | CCTGGTGCTG | GATGACAGCA | AGAGGCTAGC | CAAGAGGAAG |
| 790 | 800 | 810 | 820 | 830 | 840 |
| CTGATAGAAG | AGAACCGTGA | GAAGAGGCGG | CGGGAAGAGC | TACAGAAATC | CATTGGGCAT |
| 850 | 860 | 870 | 880 | 890 | 900 |
| AAGCCAGAGC | CCACGGATGA | GGAATGGGAG | CTCATCAAGA | CAGTCACCGA | GGCCCACGTG |
| 910 | 920 | 930 | 940 | 950 | 960 |
| GCCACCAATG | CCCAGGGCAG | CCACTGGAAG | CAGAAGCGGA | AATTTCTGCC | TGAAGACATT |
| 970 | 980 | 990 | 1000 | 1010 | 1020 |
| GGACAAGCAC | CCATTGTGAA | CGCCCCGGAA | GGTGGCAAGG | TTGATCTGGA | AGCCTTCAGC |
| 1030 | 1040 | 1050 | 1060 | 1070 | 1080 |
| CATTTTACAA | AAATCATCAC | ACCAGCAATC | ACCAGAGTGG | TGGATTTCGC | CAAAAAGTTG |
| 1090 | 1100 | 1110 | 1120 | 1130 | 1140 |
| CCCATGTTTT | GTGAGCTGCC | CTGTGAAGAC | CAGATCATCC | TCCTCAAAGG | CTGCTGCATG |
| 1150 | 1160 | 1170 | 1180 | 1190 | 1200 |
| GAGATCATGT | CCCTCCGAGC | TGCTGTGCGC | TATGACCCAG | ACAGCGAGAC | TCTAACCTTG |
| 1210 | 1220 | 1230 | 1240 | 1250 | 1260 |
| AATGGGGAAA | TGGCAGTGAC | ACGGGGCCAG | CTGAAAAACG | GAGGTCTTGG | GGTGGTGTCA |
| 1270 | 1280 | 1290 | 1300 | 1310 | 1320 |
| GATGCGATCT | TTGACCTGGG | CATGTCTCTG | TCGTCTTTCA | ACCTGGATGA | CACGGAGGTT |
| 1330 | 1340 | 1350 | 1360 | 1370 | 1380 |
| GCCCTGCTTC | AAGCCGTCCT | GCTGATGTCT | TCAGATCGCC | CAGGGCTAGC | TTGTGTTGAG |
| 1390 | 1400 | 1410 | 1420 | 1430 | 1440 |
| AGAATTGAGA | AATACCAAGA | CAGTTTCCTG | TTGGCCTTTG | AACACTATAT | CAATTACCGG |
| 1450 | 1460 | 1470 | 1480 | 1490 | 1500 |
| AAGCACCATG | TGACACACTT | TTGGCCCAAA | CTCCTGATGA | AGGTGACGGA | CCTGCGGATG |
| 1510 | 1520 | 1530 | 1540 | 1550 | 1560 |
| ATTGGAGCGT | GCCACGCCAG | CCGCTTCCTG | CACATGAAGG | TGGAGTGCCC | CACCGAGCTC |
| 1570 | 1580 | 1590 | 1600 | 1610 | 1620 |
| TTCCCGCCTC | TCTTCTTGGA | AGTCTTTGAG | GAC]TGAACGG | ACTGGACAGG | TTCTTGTCAT | coding region ends

| 1630 | 1640 | 1650 | 1660 | 1670 | 1680 |
|---|---|---|---|---|---|
| TCCTGCAGCA | CGACTGGGTG | TCGCTGCATT | CCACCTGTAG | CTCTTTCTGT | TGTCGTTTCT |
| 1690 | 1700 | 1710 | 1720 | 1730 | 1740 |
| TCGTTTCTTT | GTGTCAAGTG | AGCTCATCAG | TGGGTCAGCG | GGTCATCAGT | GGCATAGACT |
| 1750 | 1760 | 1770 | 1780 | 1790 | 1800 |
| TGGATGAAGT | GGTCCTTTGA | ATGTGGGTCT | TTGTAACCAT | TGCGTTTCGT | TCTCCAGTCC |
| 1810 | 1820 | 1830 | 1840 | 1850 | 1860 |
| TTAGTGTGAC | GGCTTTGAGG | GGTTCACAGC | AGTGCAGGCC | GAGTGGGGCC | GATCATCTCA |
| 1870 | 1880 | 1890 | 1900 | 1910 | 1920 |
| CCAGCACCAC | GTCGTCACCA | GCTCCCATCT | GTCCCTGGGC | AGACTCAAGC | AAGCCAAATG |
| 1930 | 1940 | 1950 | 1960 | 1970 | 1980 |
| GCATTACAGA | AGACTAAAGA | AGCCTTAAAA | CCGAGACGAC | AGTCATCTTG | ATCCAATGCG |
| 1990 | 2000 | 2010 | 2020 | 2030 | 2040 |
| ATCCAGTTCT | GTTGTTTGTA | AGGTGAAGCT | GGCAGAGCTC | AGGCCACCTC | AGGTTGGGCG |
| 2050 | 2060 | 2070 | 2080 | 2090 | 2100 |
| TGGCTTTTGG | CGCGTGAGGG | GAGGAGCCGT | TCCAGCTTCA | GGAACTCACA | GCTACTCAGG |
| 2110 | 2120 | 2130 | 2140 | 2150 | 2160 |
| AGCTTACCGC | TTCCAGCACC | CTTACTCTCC | AAGCAGGCTG | ACTTGGAATG | TGCAGGATAC |

TABLE I-continued

| 2170 | 2180 | 2190 | 2200 | 2210 | 2220 |
|---|---|---|---|---|---|
| CCACACCATA | ACAAATCGAC | GTTACTTTCC | ATGGCCTTCT | GTAACCTTGT | GATTTACTTC |
| 2230 | 2240 | 2250 | 2260 | 2270 | 2280 |
| AAGTTGCGCA | AGAGTAGAAC | TTGGAGACTT | GACTGGTTTG | AGGCCACAAG | GAAAGTCTCC |
| 2290 | 2300 | 2310 | 2320 | 2330 | 2340 |
| TTTTCAGGAT | GCCCATAGAG | CTTGGAAATC | ATCCATGTTA | CAGCATAGTT | TCCAAAAATG |
| 2350 | 2360 | 2370 | 2380 | 2390 | 2400 |
| GTGTTACCTC | AAGCAGGAAG | GCACCTTTGC | AGCTTAGATA | GATTCACAAG | CCATTCCCAC |
| 2410 | 2420 | 2430 | 2440 | 2450 | |
| AGAGCTCAAA | CCTGTTTACA | GAGTGCCGTC | CCTCTTCCCG | GAATTCCCGG | GG |

TABLE II

|  | 10 | 20 |
|---|---|---|
| Met Cys Met Asp Val Arg Cys Pro Ser Ile Cys Thr Ala Pro Gly Ser Arg Gly Leu Ala | | |
|  | 30 | 40 |
| Met Ala Cys Met Glu Arg Val Cys Ile Cys Lys Ala Gly Leu His Leu Asp Thr Lys Met | | |
|  | 50 | 60 |
| Asn Tyr Cys Met Peo Glu Val His Glu Gly Cys Pro Ala Ala Gly Ser Asn Arg Tyr Met | | |
|  | 70 | 80 |
| Gln Val Thr Asp Tyr Leu Ala Tyr Leu Glu Asp Ser Pro Ala Tyr Ser Gly Cys Asp Val | | |
|  | 90 | 100 |
| Gln Ala Val Pro Gly Ser Ser Ile Tyr Leu Glu Gln Ala Trp Thr Leu Asn Gln Pro Tyr | | |
|  | 110 | 120 |
| Thr Cys Ser Tyr Pro Gly Asn Leu Phe Lys Ser Lys Asp Ser Asp Leu Asp Met Ala Leu | | |
|  | 130 | 140 |
| Ser Gln Tyr Ser Gln Pro Ala His Leu Pro Glu Glu Lys Pro Phe Pro Gln Val Arg Ser | | |
|  | 150 | 160 |
| Pro Pro His Ser His Lys Lys Gly Tyr Ile Pro Ser Tyr Leu Asp Lys Asp Glu Leu Cys | | |
|  | 170 | 180 |
| Val Val Cys Gly Asp Lys Ala Thr Gly Tyr His Tyr Arg Cys Ile Thr Cys Glu Gly Cys | | |
|  | 190 | 200 |
| Lys Gly Phe Phe Arg Arg Thr Ile Gln Lys Ser Leu His Pro Ser Tyr Ser Cys Lys Tyr | | |
|  | 210 | 220 |
| Glu Gly Lys Cys Ile Ile Asp Lys Val Thr Arg Asn Gln Cys Gln Glu Cys Arg Phe Lys | | |
|  | 230 | 240 |
| Lys Cys Ile Tyr Val Gly Met Ala Thr Asp Leu Val Leu Asp Asp Ser Lys Arg Leu Ala | | |
|  | 250 | 260 |
| Lys Arg Lys Leu Ile Glu Glu Asn Arg Glu Lys Arg Arg Arg Glu Glu Leu Gln Lys Ser | | |
|  | 270 | 280 |
| Ile Gly His Lys Pro Glu Pro Thr Asp Glu Glu Trp Glu Leu Ile Lys Thr Val Thr Glu | | |
|  | 290 | 300 |
| Ala His Val Ala Thr Asn Ala Gln Gly Ser His Trp Lys Gln Lys Arg Lys Phe Leu Pro | | |
|  | 310 | 320 |
| Glu Asp Ile Gly Gln Ala Pro Ile Val Asn Ala Pro Glu Gly Gly Lys Val Asp Leu Glu | | |
|  | 330 | 340 |
| Ala Phe Ser His Phe Thr Lys Ile Ile Thr Pro Ala Ile Thr Arg Val Val Asp Phe Ala | | |
|  | 350 | 360 |
| Lys Lys Leu Pro Met Phe Cys Glu Leu Pro Cys Glu Asp Gln Ile Ile Leu Leu Lys Gly | | |
|  | 370 | 380 |
| Cys Cys Met Glu Ile Met Ser Leu Arg Ala Ala Val Arg Tyr Asp Pro Asp Ser Glu Thr | | |
|  | 390 | 400 |
| Leu Thr Leu Asn Gly Glu Met Ala Val Thr Arg Gly Gln Leu Lys Asn Gly Gly Leu Gly | | |
|  | 410 | 420 |
| Val Val Ser Asp Ala Ile Phe Asp Leu Gly Met Ser Leu Ser Ser Phe Asn Leu Asp Asp | | |
|  | 430 | 440 |
| Thr Glu Val Ala Leu Leu Gln Ala Val Leu Leu Met Ser Ser Asp Arg Pro Gly Leu Ala | | |
|  | 450 | 460 |
| Cys Val Glu Arg Ile Glu Lys Tyr Gln Asp Ser Phe Leu Leu Ala Phe Glu His Tyr Ile | | |
|  | 470 | 480 |
| Asn Tyr Arg Lys His His Val Thr His Phe Trp Pro Lys Leu Leu Met Lys Val Thr Asp | | |
|  | 490 | 500 |
| Leu Arg Met Ile Gly Ala Cys His Ala Ser Arg Phe Leu His Met Lys Val Glu Cys Pro | | |
|  | 520 | |
| Thr Glu Leu Phe Pro Pro Leu Phe Leu Glu Val Phe Glu Asp | | |

What is claimed is:

1. A recombinant DNA molecule encoding the thyroid hormone receptor PSTHR.

2. The recombinant molecule of claim 1 wherein said molecule is a replicable vector.

3. The recombinant molecule of claim 1 wherein said DNA encoding the thyroid hormone receptor PSTHR comprises the nucleotide sequence as shown in Table I.

4. A host cell containing the vector of claim 2.

5. A purified and isolated DBA molecule encoding PSTHR and comprising the nucleotide sequence as shown in Table I.

6. A purified and isolated DNA molecule encoding PSTHR and which hybridizes under conditions of high stringency to a DNA molecule having the nucleotide sequence shown in Table I.

* * * * *